US012673121B2

(12) United States Patent
Tafti

(10) Patent No.: US 12,673,121 B2
(45) Date of Patent: Jul. 7, 2026

(54) RADIOPAQUE NANOPARTICLES FOR MEDICAL IMAGING

(71) Applicant: TRANSLATIONAL AND FUNDAMENTAL TECHNOLOGIES INSTITUTE LLC, Encino, CA (US)

(72) Inventor: Bashir Akhavan Tafti, Encino, CA (US)

(73) Assignee: TRANSLATIONAL AND FUNDAMENTAL TECHNOLOGIES INSTITUTE LLC, Encino, CA (US)

( * ) Notice: Subject to any disclaimer, the term of this patent is extended or adjusted under 35 U.S.C. 154(b) by 0 days.

(21) Appl. No.: 18/524,929

(22) Filed: Nov. 30, 2023

(65) Prior Publication Data

US 2025/0177577 A1 Jun. 5, 2025

(51) Int. Cl.
| | |
|---|---|
| *A61K 49/04* | (2006.01) |
| *A61K 9/50* | (2006.01) |
| *A61K 9/51* | (2006.01) |

(52) U.S. Cl.
CPC ........ *A61K 49/0438* (2013.01); *A61K 9/5031* (2013.01); *A61K 9/5123* (2013.01); *A61K 9/5138* (2013.01); *A61K 9/5153* (2013.01); *A61K 9/5161* (2013.01); *A61K 9/5169* (2013.01)

(58) Field of Classification Search
CPC ..... A61K 9/5107; A61K 9/51; A61K 49/0438
See application file for complete search history.

(56) References Cited

U.S. PATENT DOCUMENTS

| | | |
|---|---|---|
| 6,818,199 B1 | 11/2004 | Hainfeld et al. |
| 9,433,392 B2 | 9/2016 | Ohishi |
| 9,597,419 B2 | 3/2017 | Fritz et al. |
| 9,738,596 B2 | 8/2017 | Thaning |
| 10,058,633 B2 | 8/2018 | Ferrari et al. |
| 11,207,104 B2 | 12/2021 | Mullaney et al. |
| 11,712,487 B2 | 8/2023 | Tafti |
| 2003/0120355 A1 | 6/2003 | Hafeli et al. |
| 2007/0031327 A1 | 2/2007 | Luzzi et al. |
| 2009/0148385 A1 | 6/2009 | Willard et al. |
| 2011/0104052 A1 | 5/2011 | Barnett et al. |
| 2011/0176997 A1 | 7/2011 | Zhang |
| 2011/0301452 A1 | 12/2011 | Maschke et al. |
| 2012/0123189 A1 | 5/2012 | Ribbing et al. |
| 2012/0201760 A1 | 8/2012 | Tromsdorf et al. |
| 2014/0193331 A1 | 7/2014 | Naczynski et al. |
| 2015/0147276 A1 | 5/2015 | Ingber et al. |
| 2015/0202326 A1 | 7/2015 | Ohri et al. |
| 2016/0038418 A1 | 2/2016 | DeSimone et al. |
| 2016/0213793 A1 | 7/2016 | Goodman et al. |
| 2019/0328677 A1* | 10/2019 | Kim .................... C07K 16/2875 |
| 2020/0138988 A1* | 5/2020 | Tafti ........................ A61P 35/00 |
| 2024/0009332 A1 | 1/2024 | Tafti |

FOREIGN PATENT DOCUMENTS

| | | | |
|---|---|---|---|
| EP | 2331064 A1 | 6/2011 | |
| WO | WO-92/05866 A2 | 4/1992 | |
| WO | WO-1994/014478 A1 | 7/1994 | |
| WO | WO-2005/044224 A2 | 5/2005 | |
| WO | WO-2009/073193 A2 | 6/2009 | |
| WO | WO-2009/110939 A2 | 9/2009 | |
| WO | WO-2010/015824 A1 | 2/2010 | |
| WO | WO-2010/052455 A1 | 5/2010 | |
| WO | WO-2012/007456 A1 | 1/2012 | |
| WO | WO-2014/030993 A1 | 2/2014 | |
| WO | WO-2015/040128 A1 | 3/2015 | |
| WO | WO-2015/123082 A1 | 8/2015 | |
| WO | WO-2016/191247 A1 | 12/2016 | |
| WO | WO-2017158093 A1 * | 9/2017 | ........... A61K 31/713 |
| WO | WO-2019/006099 A1 | 1/2019 | |
| WO | WO-2021/044153 A1 | 3/2021 | |

OTHER PUBLICATIONS

Chatterjee et al. "Core/shell nanoparticles in biomedical applications" Advances in Colloid and Interface Science 209 (2014) 8-39 (Year: 2014).* http://www.merriamwebster.com /dictionary/derivative (Year: 2011).*

"Cancer Facts & Figures 2016," Atlanta: American Cancer Society (2016) (70 pages).

Ali-Zade, R. A., "Investigation of polymer magnetic microspheres", Colloids and Surfaces A: Physiochemical and Engineering Aspects, 225:1-3, 111-117 (Mar. 2005) (7 pages).

Altekruse et al., "Hepatocellular Carcinoma Incidence, Mortality, and Survival Trends in the United States from 1975 to 2005," J. Clin Oncol. 27(9):1485-1491 (Mar. 2009) (7 pages).

Baio et al., "Reversible activation of pH-sensitive cell penetrating peptides attached to gold surfaces," Chem Commun (Camb). 51(2):273-275 (Oct. 2015) (9 pages).

Barth et al., "Current status of boron neutron capture therapy of high grade gliomas and recurrent head and neck cancer," Radiation Oncology. 7(146):1-21 (2012) (21 pages).

Bilbao et al., "Complications of Embolization," Semin Intervent Radial, 23(2):126-142 (2006) (17 pages).

Brechbiel, M. W., "Bifunctional chelates for metal nuclides," QJ Nucl. Med. Mol. Imaging. 52(2):166-173 (Jun. 2008) (8 pages).

(Continued)

*Primary Examiner* — James W Rogers
(74) *Attorney, Agent, or Firm* — Clark & Elbing LLP

(57) ABSTRACT

The present disclosure features imaging media including a contrast agent encapsulated within a biodegradable nanoparticle matrix. The particles are sized such that they avoid excretion via urinary excretion (e.g., at least 5 nm in diameter) during an imaging procedure or an image-guided procedure. Instead, the particles are predominantly removed from circulation by the reticuloendothelial system of the liver. This results in a buildup of contrast agent in the liver, allowing for a highly specific imaging modality for liver imaging. Further, the bulk of the imaging media is excreted into the bowel, reducing in-vivo toxicity of the imaging media. Finally, because of their size, the nanoparticles of the imaging media have a higher circulation half-life.

28 Claims, 3 Drawing Sheets

(56)           References Cited

OTHER PUBLICATIONS

Dharap et al., "Tumor-specific targeting of an anticancer drug delivery system by LHRH peptide," PNAS. 102(36):12962-12967 (Sep. 2005) (6 pages).

El-Say, K.M. and El Sawy, H.S., "Polymeric nanoparticles: Promising platform for drug delivery", International Journal of Pharmaceuticals, 528:1-2, 675-691, (Jun. 2017) (17 pages).

Gijs et al., "Microfluidic applications of magnetic particles for biological analysis and catalysis", Chemical Reviews 110:3, 1518-1563, (2010) (46 pages).

Kriegel et al., "Multi-compartmental oral delivery systems for nucleic acid therapy in the gastrointestinal tract", Advanced Drug Delivery Reviews 65:6, 891-901 (Dec. 2012) (11 pages).

Liu et al., "A Brief Review of Chelators for Radiolabeling Oligomers," Materials. 3:3204-3217 (May 2010) (14 pages).

Iordache et al., "Poly(lactic-co-glycolic) acid/chitosan microsphere thin films functionalized with Cinnamomi aetheroleumand magnetite nanoparticles for preventing the microbial colonization of medical surfaces", Journal of Sol-Gel Science and Technology 73:3, 679-686 (Feb. 2015) (8 pages).

M.F. Maitz, "Applications of synthetic polymers in clinical medicine," Biosurface and Biotribology. 1:161-176 (2015) (16 pages).

Pandori et al., "Adenovirus-Microbead Conjugates Possess Enhanced Infectivity: A New Strategy for Localized Gene Delivery," Virology 299(2):204-2012 (Apr. 2002) (9 pages).

Peers et al., "Dietary Aflatoxins and Liver Cancer—A Population Based Study in Kenya," Br. J. Cancer. 27(6):473-484 (Feb. 1973) (12 pages).

Vaidya S et al., "An overview of embolic agents," Semin Intervent Radiol. 25(3):204-15 (Sep. 2008) (12 pages).

Vroman et al., "Biodegradable Polymers," Materials. 2:307-344 (Apr. 2009) (38 pages).

Xie et al., "Nanoparticle-based theranostic agents," Adv Drug Deliv Rev. 62(11): 1064-1079 (Aug. 2010) (32 pages).

"Microparticle," Wikipedia. Wikimedia Foundation, <https://en.wikipedia.org/wiki/Microparticle>, accessed Jan. 2016 (6 pages).

Currie, Geoffrey M., "Pharmacology, Part 5: CT and MRI Contrast Media", J. Nucl. Med. Technol. 47(3): 189-202 (Sep. 2019) (14 pages).

Gessner et al., "Nanoparticles Modified with Cell-Penetrating Peptides: Conjugation Mechanisms, Physicochemical Properties, and Application in Cancer Diagnosis and Therapy," Int J Mol Sci. 21(7):2536 (Apr. 2020) (21 pages).

Guidoccio et al., "Novel Radiopharmaceuticals for Therapy," Nuclear Oncology. 217-43 (2016).

Zhao et al., "Synthetic nanoparticles for delivery of radioisotopes and radiosensitizers in cancer therapy," Cancer Nanotechnol. 7(1):9 (Nov. 2016) (23 pages).

"5-Amino-N,N-bis(2,3-dihydroxypropyl)-2,4,6-triiodoisophthalamide", CAS Common Chemistry, https://commonchemistry.cas.org/detail?cas_rn=76801-93-9 (retrieved Jun. 30, 2025) (CAS RN: 76801-93-9).

"Iohexol Related Compound B", Millipore Sigma, https://www.sigmaaldrich.com/US/en/substance/iohexolrelatedcompoundb7050276801939, (retrieved Jun. 30, 2025) (CAS RN: 76801-93-9).

"5-Amino-N,N'-bis(2,3-dihydroxypropyl)-2,4,6-triiodoisophthalamide", CAS Common Chemistry, https://commonchemistry.cas.org/detail?cas_rn=76801-93-9 (retrieved Jun. 30, 2025) (CAS RN: 76801-93-9) (3 pages).

"Iohexol Related Compound B", Millipore Sigma, https://www.sigmaaldrich.com/US/en/substance/iohexolrelatedcompoundb7050276801939, (retrieved Jun. 30, 2025) (CAS RN: 76801-93-9) (2 pages).

* cited by examiner

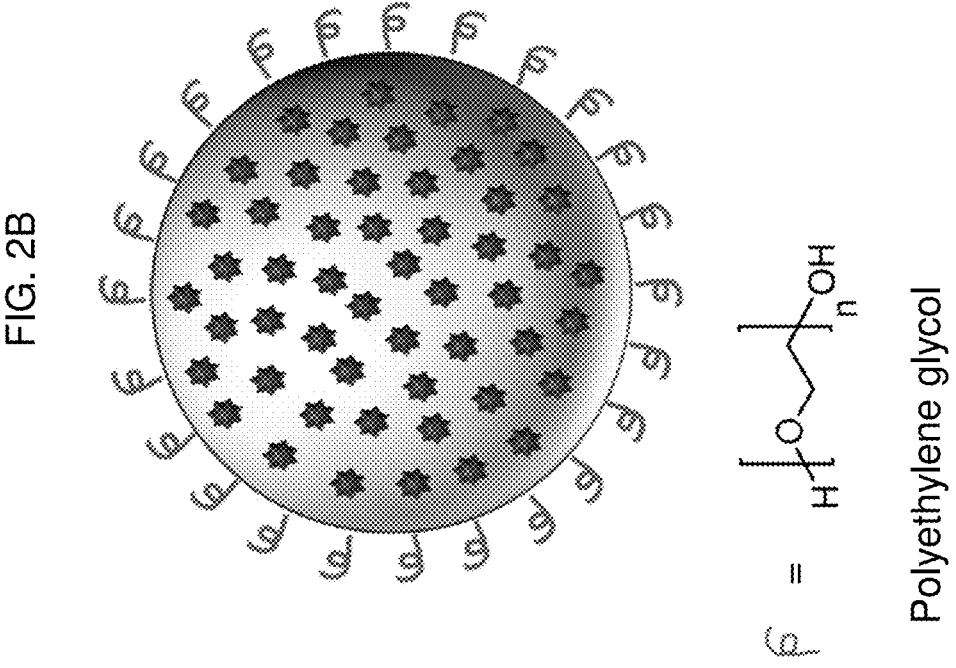
FIG. 2A
FIG. 2B
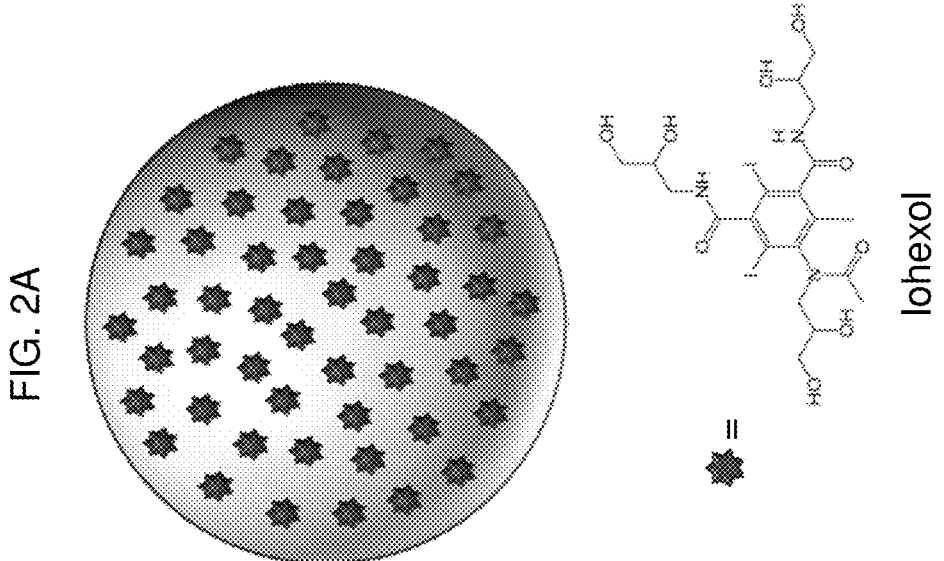
Iohexol
Polyethylene glycol

FIG. 3C
FIG. 3B
FIG. 3A
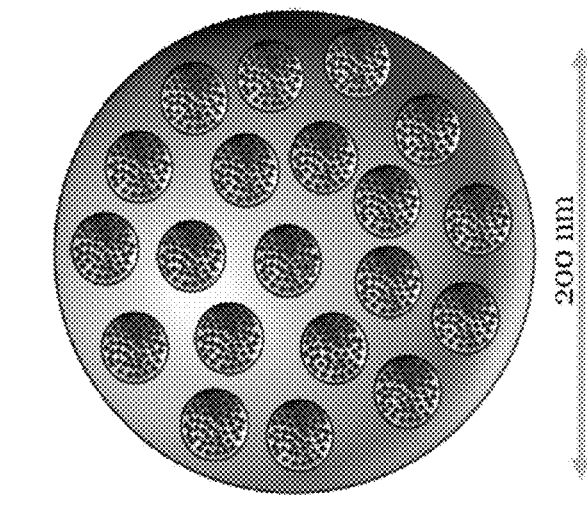
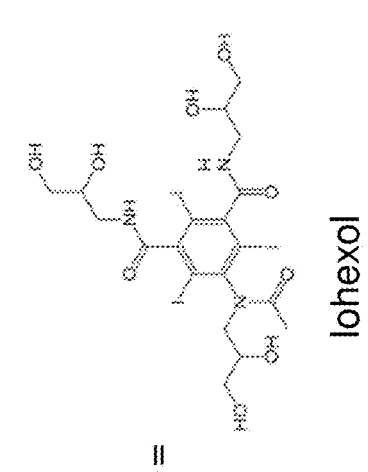
Polyethylene glycol
200 nm
10 nm
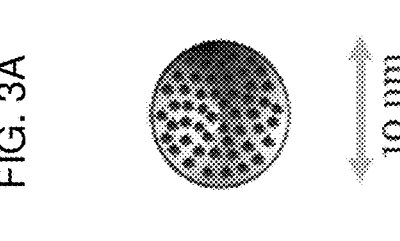
Iohexol

RADIOPAQUE NANOPARTICLES FOR MEDICAL IMAGING

BACKGROUND

X-ray based imaging modalities such as computed tomography (CT) and fluoroscopy play a pivotal role in diagnosis and treatment of a plethora of disease and other medical conditions. These imaging modalities frequently include a contrast agent that enhances the visibility of anatomical structures and better differentiates between tissues of similar composition.

The currently available contrast agents have several major risks and limitations, such as a high risk of nephrotoxicity resulting in renal failure (particularly for patients with renal diseases and diabetes) and rapid contrast agent washout. Rapid washout can be particularly problematic for liver imaging. For example, cancer imaging protocols often require delayed imaging (i.e. imaging several minutes after contrast administration). However, current contrast agents are rapidly washed out of the liver before successful imaging is completed. Another example is during biopsy or ablation procedures when a biopsy needle or ablation probe needs to be accurately placed within a target tumor. In many such instances, the tumor is isodense to the normal liver parenchyma and cannot be differentiated from normal tissue. Although contrast injection can make these tumors visible for a very short period of time (approximately 90 seconds), contrast residence time in the liver is not long enough for accurate needle or probe placement as the latter tasks take several minutes (approximately 10-15 minutes for each probe). Repeat contrast injection is not an option as higher doses of contrast are associated with risks including metabolic derangements and nephrotoxicity.

Therefore, there is a need in the art for contrast agents and imaging media with lower nephrotoxicity, higher circulation half-life, and higher liver-residence time.

SUMMARY OF THE DISCLOSURE

The present disclosure features imaging media including a contrast agent (e.g., iodine-containing molecules such as iohexol) encapsulated within a nanoparticle, in which the nanoparticle includes or is formed with a biodegradable polymer matrix. The particles are sized such that they avoid urinary excretion during an imaging procedure or image-guided procedure (e.g., the nanoparticles have a size of at least 5 nm in diameter). Instead, the particles are predominantly removed from circulation by the reticuloendothelial system of the liver and excreted through the biliary system into the bowel. This results in a buildup of contrast agent in the liver, allowing for a highly specific imaging agent for liver imaging. Further, the bulk of the iodine content is excreted into the bowel. Consequently, the imaging media of the present disclosure minimizes renal toxicity when used in vivo. Finally, because of their size, the nanoparticles of the imaging media have a longer circulation half-life and residence time in the target organ. For example, currently available liver contrast agents have a circulation half-life of about 20 minutes and a liver-residence time of from about 2 to 3 minutes. The imaging media of the present disclosure may have a circulation half-life of at least 2 hours (e.g., at least 3 hours, at least 4 hours, at least 5 hours, at least 6 hours, or from about 4 hours to about 6 hours) and a liver-residence time of at least 15 minutes (e.g., at least 20 minutes, at least 25 minutes, at least 30 minutes, at least 35 minutes, at least 40 minutes, at least 45 minutes, at least 50 minutes, at least 55 minutes, at least 1 hour, etc.).

In a first aspect, the present disclosure features an imaging media including a nanoparticle including a biodegradable matrix, wherein the biodegradable matrix does not include a metal matrix, and a contrast agent encapsulated within the biodegradable matrix. In some embodiments, the nanoparticle includes a polymer matrix. In some embodiments, the matrix is or includes hyaluronic acid (HA), polyethylene glycol diacrylate (PEGDA), polyglycolic acid (PGA), polylactic acid (PLA), poly(lactic-co-glycolic acid) (PLGA), Collagen, Gelatin, carboxymethyl chitosan (CCN), carboxymethyl cellulose (CMC), phospholipids, a polysaccharide, or a combination thereof. In some embodiments, the diameter of the nanoparticle is from about 5 nm to about 1000 nm. In some embodiments, the diameter of the nanoparticle is about 100 nm to about 1000 nm. In some embodiments, the nanoparticle is spherical, elliptical, rod-shaped, cylindrical, prismatic, or irregular.

In some embodiments, the nanoparticle further includes a coating. In some embodiments, the coating is hydrophilic. In some embodiments, the coating is a polymer coating. In some embodiments, the polymer coating is polyglucose sorbitol carboxymethyl ether or polyethylene glycol (PEG). In some embodiments, the coating is from about 1 nm to about 100 nm thick.

In some embodiments, the nanoparticle further includes a sub-nanoparticle encapsulated within the biodegradable matrix. In some embodiments, the sub-nanoparticle is formed from or includes a biodegradable matrix. In some embodiments, the sub-nanoparticle is formed from or includes a biodegradable matrix, such as but not limited to hyaluronic acid (HA), polyethylene glycol diacrylate (PEGDA), polyglycolic acid (PGA), polylactic acid (PLA), poly(lactic-co-glycolic acid) (PLGA), Collagen, Gelatin, carboxymethyl chitosan (CCN), carboxymethyl cellulose (CMC), phospholipids, a polysaccharide, or a combination thereof. In some embodiments, the sub-nanoparticle and the nanoparticle contain an identical material. In some embodiments, the sub-nanoparticle is spherical, elliptical, rod-shaped, cylindrical, prismatic, or irregular. In some embodiments, the sub-nanoparticle is substantially spherical, and the diameter of the sub-nanoparticle is from about 1 nm to about 10 nm.

In some embodiments, the contrast agent is or includes iodine. In some embodiments, the contrast agent is a non-ionic contrast agent. In some embodiments, the contrast agent is an ionic contrast agent. In some embodiments, the contrast agent is encapsulated within the biodegradable matrix of the nanoparticle. In some embodiments, the contrast agent is iodixanol, iohexol, iohexol related compound B or a derivative thereof, diatrizoic acid or a derivative thereof, or a combination thereof.

In a second aspect, the disclosure features a pharmaceutical composition containing the imaging media of the first aspect and a pharmaceutically acceptable excipient. In some embodiments, the contrast agent includes iodine and the pharmaceutical composition includes iodine at a concentration of from about 5 mg/mL to about 350 mg/mL. In some embodiments, the contrast agent includes iodine and the pharmaceutical composition includes iodine at a concentration of from about 5 mg/mL to about 100 mg/mL. In some embodiments, the excipient is a polyol (e.g., polyethylene glycol), a polyether, salcaprozate sodium, or sodium caprate.

In a third aspect, the disclosure features a method of imaging biological tissue in a subject (e.g., the liver) by administering the imaging media of the first aspect or the pharmaceutical composition of the second aspect to the subject and performing an imaging or an image-guided procedure. In some embodiments, the biological tissue is an organ (e.g., the liver, heart, brain, kidneys, and lungs). In some embodiments, the imaging media or pharmaceutical composition is administered directly to the biological tissue. In some embodiments, the imaging media or pharmaceutical composition is administered intravascularly. In some embodiments, the imaging procedure is an X-ray-based imaging procedure. In some embodiments, the X-ray imaging procedure is fluoroscopy or computed tomography (CT) imaging. In some embodiments, the imaging media provides an enhancement of at least 10 Hounsfield units (HU), such as, e.g., 10-150 HU (e.g., about 20 HU, about 30 HU, about 40 HU, about 50 HU, about 60 HU, about 70 HU, about 80 HU, about 90 HU, or about 100 HU), in the target organ as compared to an imaging procedure performed in the absence of the imaging media. In some embodiments, the method includes mixing the nanoparticle and the excipient at the time of administration.

In a fourth aspect, the disclosure features a kit including the imaging media of the first aspect, or the pharmaceutical composition the second aspect. In some embodiments, the imaging media and the excipient are provided separately. In some embodiments, the imaging media is provided as a lyophilized powder. In some embodiments, the kit includes a mixer. In some embodiments, the kit includes a puncture set. In other embodiments, the kit includes instructions for administering the imaging media and/or pharmaceutical composition to a subject in need thereof, e.g., for imaging a biological tissue (e.g., the liver).

Definitions

To facilitate an understanding of this disclosure, a number of terms are defined below. Terms defined herein have meanings as commonly understood by a person of ordinary skill in the areas relevant to the disclosure. Terms such as "a," "an," and "the" are not intended to refer to only a singular entity but include the general class of which a specific example can be used for illustration. The terminology herein is used to describe specific embodiments of the disclosure, but their usage does not limit the disclosure, except as outlined in the claims.

As used herein, the term "about" refers to a value that is within ±10% of the value being described.

The terms "administering" or "administration" mean deployment of a composition (e.g., an imaging media described herein) to a target site (e.g., the liver) for treatment and/or diagnosis. Administration may refer to, e.g., parenteral administration. As used herein, "parenteral administration" refers to administration of a composition characterized by physical breaching of the tissue of a subject and administration of the pharmaceutical composition through the breach in the tissue. Parenteral administration includes, but is not limited to, administration of a pharmaceutical composition by injection of the composition, by application of the composition through a surgical incision, by application of the composition through a tissue-penetrating non-surgical wound, and the like. Parenteral administration is contemplated to include intravascular administration, subcutaneous administration, intraperitoneal administration, intramuscular administration, and intraosseous administration. In a preferred embodiment, administration is intravascular administration.

By "biodegradable," as used herein, is meant any material which the body of a subject is capable of removing by breaking down the material (e.g., by metabolic degradation, absorption, phagocytosis, or enzymatic digestion) and/or by filtering the material out of the body (e.g., via the kidney or liver) and excreting it from the body (e.g., via the bowel). Biodegradable materials may also be considered non-toxic.

By "circulation lifetime" is meant the time for which an administered material remains in the body of a subject. A circulation lifetime may be measured by the "circulation half-life," e.g., the time it takes for half of an administered composition (e.g., half of the total mass of nanoparticles administered to a subject) to be removed from the body of a subject (e.g., via urinary excretion or bowel excretion).

By "metal matrix" is meant any chemical composition forming a structure, in which the chemical matrix includes at least one metal atom or metal ion covalently bound or metallically bound to one or more other atoms or ions in the matrix.

By "polymer matrix" is meant any chemical composition forming a structure, in which the chemical matrix includes a polymeric organic material. Polymeric organic materials include polyglycolide (PGA), polylactide (PLA), poly(lactide-co-glycolide) (PLGA), polycaprolactone (PCL), poly (alkenedicarboxylate)s (e.g., poly(butylene succinate) (PBS), poly(ethylene succinate) (PES), poly(butylene succinate-co-adipate) (PBSA), or poly(p-dioxanone) (PPDO)), polycarbonates (e.g., poly(trimethylene carbonate) (PTMC), poly(propylene carbonate), or poly[oligo(tetramethylene succinate)-co(tetramethylene carbonate)]), aromatic copolyesters (e.g., poly(butylene adipate-co-terephtalate) (PBAT), poly(ethylene terephtalate), BIOMAX®, ECOFLEX®, ORIGO-BI®, poly($\beta$-hydroxyalcanoate), xanthan, curdlan, pullulan, poly(hydroxybutyrate) (PHB), or poly(hydroxybutyrate-co-hydroxyvalerate) (PHBV)), polyamides and polypeptides (e.g., aliphatic poly(ester-amide)s, copolymers of 1,2-ethanediol, adipic acid and amino acids (including glycine and phenylalanine), CAMEO®, or BAK 1095®), polyanhydrides (e.g., poly(sebacic anhydride)), polysaccharides e.g., (chitin, chitosan, starch, poly-$\alpha$-1,4-D-glucopyranoside (amylose), poly-$\alpha$-1,4-Dglucopyranoside-$\alpha$-1,6-D-glucopyranoside (amylopectine), cellulose, cellulose esters, cellulose acetate, microcrystalline cellulose, carboxymethylcellulose, lignocellulose, alginic acid, sodium alginate, calcium alginate, hyaluronic acid, or chondroitin sulphate), proteins (e.g., gelatin, gelatine grafts, soy protein, wheat gluten, collagen, elastin, albumine, or fibrin), oils, fatty acids, methyl methacrylate poly(ethyl acrylate), polymer blends (e.g., starch blends (e.g., starch-poly(ethylene-co-vinyl alcohol) (EVOH), starch-polyvinyl alcohol, starch-PLA, starch-PCL, starch-PBS, or starch-PHB), blends of PHBV and PPC, blends of poly(aspartic acid-co-lactide) (PAL) and PLLA, blends of PAL and PBS, or blends of PAL and PCL), poly(propylene fumarate) (PPF), poly(E-caprolactone-fumarate), or any copolymer, block-copolymer, dendrimer, or mixture thereof.

By "residence time" is meant the time for which an administered material (e.g., a nanoparticle) remains in a portion of a subject. The residence time may be an organ-residence time (i.e., the residence time of the administered material in an organ; e.g., a liver-residence time). The residence time may be given as the "residence half-life," or the time it takes for half of a composition localized to a portion of a subject (e.g., half of the total mass of nanoparticles in the liver of a subject) to be removed from said portion. The administered material being removed from the portion of the subject may include excretion of the material (e.g., via urinary excretion or bowel excretion), or the movement of the administered material into a second portion of the subject (e.g., into the vasculature of the subject, into a second organ of the subject, etc.). In preferred embodiments, the residence time refers to a "liver-residence time," e.g., the length of time an administered material remains in the liver of a subject.

By "treating" or "treatment" is meant the medical management of a subject with the intent that an amelioration, repair, or prevention of a further injury, disease, pathological condition, or disorder will result. Treatment or treating includes, e.g., the identification of a lesion in an organ, and any subsequent medicaments or surgeries provided. Treatment or treating includes: active treatment, that is, treatment directed specifically toward improvement of the injury or disease, pathological condition, or disorder, and also includes causal treatment, that is, treatment directed toward removal of the cause of the injury or disease, pathological condition, or disorder. In addition, this term includes palliative treatment, that is, treatment designed for the relief of symptoms rather than the curing of the injury or disease, pathological condition, or disorder; preventive treatment, that is, treatment directed to prevention of the injury or disease, pathological condition, or disorder; and supportive treatment, that is, treatment employed to supplement another specific therapy directed toward the improvement of the injury or disease, pathological condition, or disorder.

As used herein, any values provided in a range of values include both the upper and lower bounds, and any values contained within the upper and lower bounds.

BRIEF DESCRIPTION OF THE DRAWINGS

FIG. 1A shows a computed-tomography contrast image generated without a contrast agent. FIG. 1B shows a computed-tomography contrast image of the same liver as in FIG. 1A that was generated in the presence of a contrast agent. The black box in FIG. 1B encloses a shaded region, signaling the presence of a liver tumor. The region enclosed by the black box in FIG. 1A is indistinguishable from the tissue around it. In the absence of a contrast agent, the tumor would be undetectable via computed tomography.

FIGS. 2A-2B show the structure of exemplary imaging media of the present disclosure. FIG. 2A shows a schematic illustrating the encapsulation of a contrast agent such as iohexol (represented by a star) within a nanosphere. FIG. 2B shows the modification of a nanoparticle of FIG. 2A with a coating material (represented by a spiral). The nanoparticle and the coating may be different materials. For example, the nanoparticle may be composed of poly(lactide-co-glycolide) (PLGA) and the coating may be composed of polyethylene glycol (PEG).

FIGS. 3A-3B is an image showing the structure of an imaging media including a sub-nanoparticle. FIG. 3A shows the structure of a single sub-nanoparticle. A contrast agent such as iohexol (represented by a star) is encapsulated by the nanosphere. FIG. 3B shows a schematic illustrating the encapsulation of a sub-nanoparticle within a nanoparticle. Leakage of the contrast agent from the imaging media is reduced by encapsulating the contrast agent only in the sub-nanoparticle, which decreases the risk of nephrotoxicity upon administration of the imaging media to a subject. The sub-nanoparticle and the nanoparticle may be made of the same material (e.g., PLGA). In an example, the diameter of the nanoparticle is approximately 20 times the diameter of the sub-nanoparticle.

FIG. 3C is an image showing the modification of a nanoparticle of FIG. 3B with a coating material (represented by a spiral). The nanoparticle and the coating may be different materials. For example, the nanoparticle may be composed of PLGA and the coating may be composed of PEG.

DETAILED DESCRIPTION

Figure 1B:
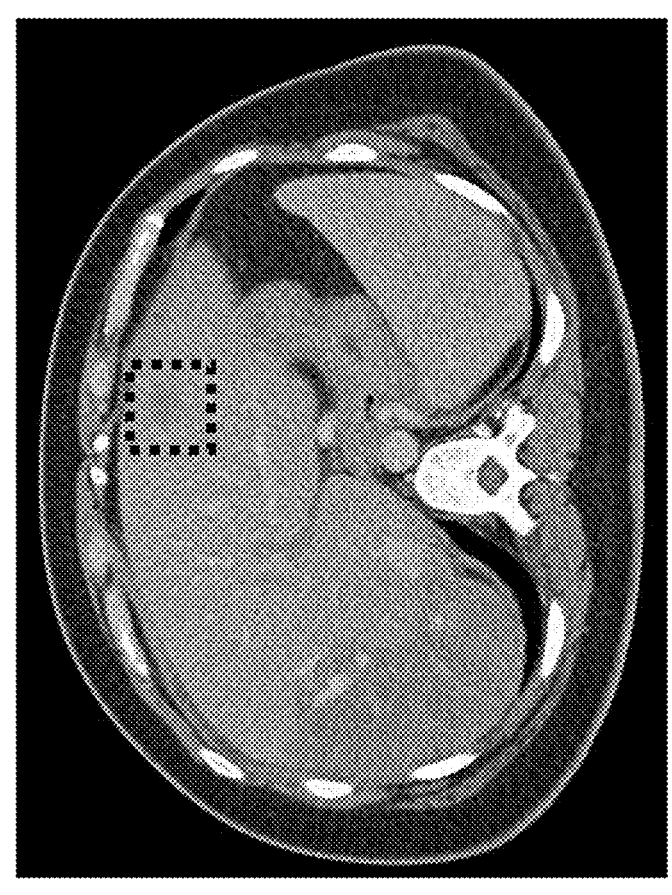
FIGS. 1A-1B show the criticality of image contrast for tumor visualization.

The present disclosure features imaging media made from a contrast agent (e.g., a contrast agent including iodine) incorporated into a nanoparticle formed from or including a biodegradable matrix. The contrast agent may be enclosed within the nanoparticle (i.e., contained on all sides by the biodegradable matrix). The nanoparticle has a size (e.g., the nanoparticle may have a diameter of at least 5 nm) that promotes excretion by a route other than urinary excretion or such that the nanoparticle undergoes urinary excretion at a lower rate relative to a nanoparticle with a smaller dimension (e.g., a diameter of less than 5 nm) or a contrast agent not enclosed within a nanoparticle. The size of the nanoparticles promotes their removal from circulation by the reticuloendothelial system of the liver and their excretion through the biliary system into the bowel, reducing the risk of nephrotoxicity. As a result, the imaging media of the present disclosure may be administered to a subject with an underlying kidney disease or other medical condition (e.g., diabetes). Further, the imaging media of the present disclosure may be administered in larger doses or administered in a greater number of doses, without provoking nephrotoxic side effects.

The size of the imaging media of the present disclosure limits or reduces urinary excretion thereof. As a result, the imaging media of the present disclosure exhibits a long circulation half-life (e.g., of at least 2 hours, at least 3 hours, at least 4 hours, at least 5 hours, at least 6 hours, or from about 4 hours to about 6 hours) and a long liver-residence time (e.g., of at least 15 minutes, at least 20 minutes, at least 30 minutes, at least 45 minutes, least 1 hour (hr), at least 1.5 hr, at least 2 hr, at least 2.5 hr, at least 3 hr, at least 3.5 hr, at least 4 hr, at least 4.5 hr, at least 5 hr, at least 5.5 hr, or at least 6 hr.). The longer circulation half-life and liver-residence time facilitate the extended visualization of target tissue that is frequently required during an image-guided procedure. For example, an image-guided procedure may include the placement of one or more ablation probes (e.g., for tumor ablation), the placement of each probe requiring approximately 10 minutes. Alternatively, an imaging procedure may include multiple diagnostic and/or therapeutic procedures (e.g., using computed tomography angiography (CTA) to image a subject for a gastrointestinal bleed, followed by additional therapeutic angiography for embolization at the site of the hemorrhage). If a contrast agent is washed out of the target organ before the procedure is completed, multiple doses of contrast agent may be required, often exposing the subject to toxic levels of contrast agent. As a result of their long circulation lifetime, a single dose of an imaging media of the present disclosure may be sufficient to complete a procedure (e.g., sufficient to orient all probes for an ablation experiment).

Imaging Modalities and Imaging Procedures

The imaging media of the present disclosure may be used in combination with an imaging modality to perform an imaging procedure. Imaging procedures are used to provide detailed information about various chemical factors (e.g., hydration state, nucleic acid stacking, ion concentrations, etc.), structural factors (e.g., bone fractures or breaks, muscle damage, etc.), or biological factors (e.g., cellular structure, disease progression, lesion or tumor formation, etc.) within a subject. An imaging procedure involves stimulating a sample (e.g., the tissue of a subject) with, e.g., electromagnetic radiation (e.g., UV-light, X-ray light, microwave light, radio wave light, etc.). Different atoms, molecules, and/or cells of the sample then respond differently to the stimulation (e.g., scattering, absorbing, fluorescing, or transmitting light), depending on their local chemical or biological environment. This difference in response is then detected by a detector and processed into an image displaying the response of the sample across a range of locations. The ability of an imaging procedure to resolve differences in signal strength at different locations may be limited by a combination of the signal strength at the target location, the variability in signal strength between the target location and neighboring locations, and the capability of the detector to resolve differences in signal strength at different locations.

Figure 1A:
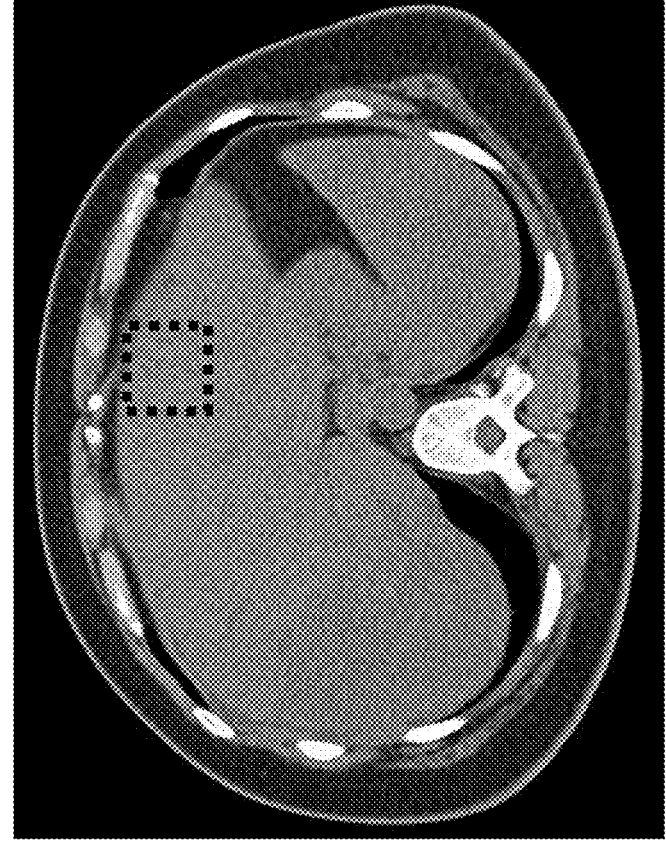

The imaging media of the present disclosure may promote an increase in the strength of a signal at a target tissue detected during an imaging procedure (e.g., by accumulating in higher concentrations and/or by remaining resident in the target tissue for an extended period of time, such as from 20 minutes to up to six hours) or may increase the variability in signal strength between two nearby locations. For example, imaging of liver tissue to detect tumors in the absence of imaging media is often hindered by the isodensity of liver tissue and tumor tissue. In such situations, the imaging media of the present disclosure may be administered to improve the signal difference between the target tissue (e.g., tumor tissue) and nearby tissue (e.g., healthy liver tissue). For example, FIG. 1 shows a computed tomography image of a liver both without (FIG. 1A) and with (FIG. 1B) a contrast agent. The region enclosed by the black box in FIG. 1B shows a clear shadowing—indicative of tumorous tissue. In contrast, the same region of tissue imaged without a contrast agent in FIG. 1A is nearly indistinguishable from the tissue around it.

The imaging media of the present disclosure may be used in an imaging modality selected from the group consisting of magnetic resonance imaging, ultrasonic imaging, optical imaging (e.g., visible 2D-3D imaging), optical coherence tomography (e.g., hyper-spectral imaging, polarized light imaging, Raman imaging, and fluorescence imaging), electrophysiology, X-ray imaging (e.g., computed tomography and X-ray fluoroscopy), photo-acoustic imaging, positron emission tomography, thermal imaging, electromechanical arrays (strain gauges, ionic conductors), and biosensor arrays. The imaging modality may include a combination of two or more imaging modalities, also referred to as "dual-modality imaging" or "hybrid modality" in the art.

The imaging modality may be, for example, X-ray imaging. X-ray imaging proceeds by exposing a subject to X-ray photons (e.g., photons of from about 124 keV to about 145 keV). X-rays are then absorbed by some biological tissues, while passing through others with minimal interactions. The signal observed is the attenuation of X-rays by biological tissue. The degree of attenuation is measured in "Hounsfield Units" (HU), which measures the relative radiodensity of the imaged location compared to distilled water (definitionally set to 0 HU) and air (definitionally set at −1000 HU) at standard temperature and pressure. Accordingly, a change in signal attenuation of 1 HU corresponds to an X-ray attenuation of approximately 0.1% of the X-ray attenuation of water. High density biological tissue (e.g., bones, tumors, and solid organs, such as the liver) typically have a larger X-ray attenuation then surrounding tissue, making them ideal targets for X-ray-based imaging modalities. However, the similar X-ray attenuations of the liver and tumorous liver tissue make precise identification and characterization via X-ray imaging of the tumorous tissue more difficult. The imaging media of the present disclosure may provide an image contrast of at least 10 HU (e.g., at least 20 HU, at least 30 HU, at least 40 HU, at least 50 HU, at least 60 HU, at least 70 HU, at least 80 HU, at least 90 HU, or at least 100 HU) in the target organ as compared to an image taken without the contrast agent.

During an imaging or image-guided procedure, a subject is administered the imaging media of the disclosure (e.g., as a part of a pharmaceutical composition). A duration is provided for the imaging media to circulate in the subject's body. During this duration, the imaging media may localize to an organ (e.g., the liver). The duration may be less than 5 minutes (e.g., less than 4 minutes, less than 3 minutes, less than 2 minutes, less than 1.5 minutes, less than 1 minute, or less than 0.5 minutes). The duration may change depending on the route of administration. After the duration, an imaging procedure may then be used to image the subject (e.g., image the liver of the subject), whereby the imaging media enhances the radiodensity of a target tissue or structure, thereby assisting in diagnosing and/or treating the subject.

An imaging procedure may be followed by a treatment procedure (e.g., an ablation procedure). The treatment procedure may include, e.g., the alignment of one or more probes with an imaged tumor. During a treatment procedure, the imaging procedure may be repeated in order to optimally align or orient a medical device, e.g., an ablation probe, with a site in the subject, e.g., a tumor.

Contrast Agents

Contrast agents are compounds which improve the image contrast (e.g., the difference in signal strength from a target tissue and tissue proximal thereto) of an image obtained from an imaging procedure. A common problem encountered during an imaging procedure is that the difference in signal between different chemical or biological environments is too weak to be observed. Contrast agents serve to change the relative signal differences observed in an imaging procedure, either by increasing, decreasing, or otherwise modulating the signal. For example, an X-ray contrast agent may have a larger X-ray attenuation than the biological tissue to be imaged, causing a larger X-ray attenuation of tissue which has absorbed contrast agent. A contrast agent works through selective uptake of the contrast agent by a certain tissue or region of tissues of the sample.

In an imaging procedure, it is desirable for the contrast agent to be specifically absorbed by or to accumulate in a particular organ of the body (e.g., the liver, the brain, the intestines, the kidney, the ureters, the bladder, etc.). This allows for the specific, high contrast imaging of the desired organ. Yet, it is difficult for certain organs, such as the liver, to build up a large enough concentration of the contrast agent to be imaged due to the short residence time of most contrast agents known in the art in the target organ (e.g., a short residence time in the liver). Further, contrast agents, particularly in large doses, are frequently toxic to a subject. Common side effects of administering contrast agents include anaphylactoid reactions, contrast-induced nephropathy, and hyperthyroidism. It is therefore important that any imaging media including a contrast agent be minimally toxic and biodegradable.

Contrast agents featured in the present disclosure are encapsulated by or imbedded in a biodegradable matrix of an imaging media, thereby containing the contrast agent and preventing the non-specific release of the contrast agent throughout the body. The size of the nanoparticle may be selected such that the imaging media is selectively absorbed by a specific organ (e.g., the liver or the kidney) or a specific type of tissue (e.g., a tumor), or is specifically excluded by an organ or type of tissue. For example, the nanoparticle may be greater than 5 nm in diameter, thereby excluding urinary excretion and causing buildup of the imaging media in the liver. This causes accumulation of contrast agent in the liver, allowing for a highly specific imaging modality for liver imaging. The particles are then predominantly removed from circulation by the reticuloendothelial system of the liver and excreted through the biliary system into the bowel. This minimizes renal toxicity, given that the bulk of the contrast agent is excreted into the bowel.

The contrast agent may be an X-ray contrast agent (also referred to as a radiocontrast agent), such as iodine. Iodine is particularly amenable to x-ray imaging, due in part to the X-ray energies required to excite the core electrons (i.e., "k-shell" or "1 s" electrons) of Iodine overlapping with the average energy of x-rays used in radiology, resulting in optimum attenuation of x-ray beams.

The X-ray contrast agent may also be one that includes a nonionic iodine compound (e.g., iodixanol, iohexol, iohexol related compound B or a derivative thereof, diatrizoic acid or a derivative thereof, or a combination thereof) The X-ray contrast agent may also be or includes an ionic iodine compound (e.g., a diatrizoate salt, an iothalamate salt, or a salt of any nonionic iodine compound.). The concentration of the contrast agent may be given as the concentration of iodine per mL of a pharmaceutical composition administered to the subject. For example, the contrast agent may be from about 2 mg of iodine per mL of pharmaceutical composition to about 340 mg of iodine per mL of pharmaceutical composition (e.g., from about 3 mg/mL to about 300 mg/mL, from about 4 mg/mL to about 260 mg/mL, from about 5 mg/mL to about 220 mg/mL, from about 10 mg/mL to about 180 mg/mL, from about 25 mg/mL to about 140 mg/mL, or from about 50 mg/mL to about 100 mg/mL).

Exemplary iodine-based contrast agents include iohexol, iodixanol, ioversol, iopamidol, ioxilan, iopromide, iobitridol, iopamidol, triiodated aromatic rings, and lipiodol. Additional contrast agents are known in the art, see, e.g., U.S. Pat. Nos. 6,818,199; 9,433,392; 9,597,419; 9,694,742; and 9,738,596; and International Patent Publication No.: WO 2012/007456; WO 1994/014478; WO 2021/044153; and WO 2015/040128, the contrast agents of which are incorporated herein by reference.

Nanoparticles

The present disclosure features imaging media including a nanoparticle made from a biodegradable matrix. The biodegradable matrix defines the structure (e.g., the size or shape) of the nanoparticle. The biodegradable matrix may form a core (e.g., a core made of a material, e.g., a polymer core or a metal-containing core) into which the contrast agent may be encapsulated. The nanoparticle may be substantially spherical, elliptical, rod-shaped, cylindrical, or prismatic or the nanoparticle may be irregularly shaped. The diameter of the nanoparticle may be, e.g., at least 5 nm (e.g., at least 10 nm, at least 15 nm, at least 20 nm, at least 25 nm, at least 30 nm, at least 35 nm, at least 40 nm, at least 50 nm, at least 75 nm, at least 100 nm, at least 125 nm, at least 150 nm, at least 175 nm, at least 200 nm, at least 250 nm, at least 300 nm, at least 350 nm, at least 400 nm, at least 450 nm, at least 500 nm, at least 550 nm, at least 600 nm, at least 650 nm, at least 700 nm, at least 800 nm, or at least 900 nm). For example, the nanoparticle may have a diameter within the range of about 5 nm to about 1000 nm (e.g., from about 10 nm to about 1000 nm, from about 20 nm to about 1000 nm, from about 30 nm to about 1000 nm, from about 40 nm to about 1000 nm, from about 50 nm to about 1000 nm, from about 75 nm to about 1000 nm, from about 100 nm to about 1000 nm, from about 10 nm to about 900 nm, from about 15 nm to about 800 nm, from about 20 nm to about 700 nm, from about 25 nm to about 650 nm, from about 30 nm to about 600 nm, from about 35 nm to about 550 nm, from about 40 nm to about 500 nm, from about 45 nm to about 450 nm, or from about 50 nm to about 400 nm). The imaging media may have a combination of nanoparticles of different diameters. The size of the nanoparticle precludes or reduces the likelihood of urinary excretion.

The biodegradable matrix may be formed from or include a material that may be selected to be non-toxic, biocompatible, hydrophobic, and/or hydrophilic. The biodegradable matrix of the present disclosure may be a polymer matrix (e.g., a nanoparticle with a polymer core). Polymer matrices, as used herein, refers to any biodegradable matrix which includes at least one organic polymer. The matrix may be both polymeric and both biodegradable (e.g., the core or the nanoparticle may be a biodegradable polymer).

Biodegradable, polymeric materials that can be used to form the nanoparticles include, e.g., polyglycolide (PGA), polylactide (PLA), poly(lactide-co-glycolide) (PLGA), polycaprolactone (PCL), poly(alkenedicarboxylate)s (e.g., poly(butylene succinate) (PBS), poly(ethylene succinate) (PES), poly(butylene succinate-co-adipate) (PBSA), or poly (p-dioxanone) (PPDO)), polycarbonates (e.g., poly(trimethylene carbonate) (PTMC), poly(propylene carbonate), or poly[oligo(tetramethylene succinate)-co(tetramethylene carbonate)]), aromatic copolyesters (e.g., poly(butylene adipate-co-terephtalate) (PBAT), poly(ethylene terephtalate), BIOMAX®, ECOFLEX®, ORIGO-BI®, poly(β-hydroxyalcanoate), xanthan, curdlan, pullulan, poly(hydroxybutyrate) (PHB), or poly(hydroxybutyrate-co-hydroxyvalerate) (PHBV)), polyamide and poly(amino acid) polymers (e.g., an aliphatic poly(ester-amide), a copolymer of 1,2-ethanediol, adipic acid and amino acids (including glycine and phenylalanine), CAMEO®, or BAK 1095®), polyanhydrides (e.g., poly(sebacic anhydride)), polysaccharides e.g., (chitin, chitosan, starch, poly-α-1,4-D-glucopyranoside (amylose), poly-α-1,4-Dglucopyranoside-α-1,6-D-glucopyranoside (amylopectine), cellulose, cellulose esters, cellulose acetate, microcrystalline cellulose, carboxymethylcellulose, lignocellulose, alginic acid, sodium alginate, calcium alginate, hyaluronic acid, or chondroitin sulphate), proteins (e.g., gelatin, gelatine grafts, soy protein, wheat gluten, collagen, elastin, albumine, or fibrin), oils, fatty acids, methyl methacrylate poly(ethyl acrylate), polymer blends (e.g., starch blends (e.g., starch-poly(ethylene-co-vinyl alcohol) (EVOH), starch-polyvinyl alcohol, starch-PLA, starch-PCL, starch-PBS, or starch-PHB), blends of PHBV and PPC, blends of poly(aspartic acid-co-lactide) (PAL) and PLLA, blends of PAL and PBS, or blends of PAL and PCL), poly(propylene fumarate) (PPF), poly(E-caprolactone-fumarate), or any copolymer, block-copolymer, dendrimer, or mixture thereof. Additional biodegradable matrices are known in the art (see, e.g., U.S. Pat. No. 10,058,633; the matrices of which are incorporated herein by reference). The biodegradable matrix may be from about 20 wt % to about 99.999 wt % of the imaging media (e.g., from 40 wt % to 99.995 wt %, from 60 wt % to 99.99 wt %, from 70 wt % to 99.9 wt %, or from 80 wt % to 99 wt %). The matrix of the nanoparticle may be hyaluronic acid (HA), polyethylene glycol diacrylate (PEGDA), polyglycolic acid (PGA), polylactic acid (PLA), poly(lactic-co-glycolic acid) (PLGA), Collagen, Gelatin, carboxymethyl chitosan (CCN), carboxymethyl cellulose (CMC), a phospholipids, a polysaccharide (e.g., cellulose, dextran chitin, chitosan, pullulan, carrageenan, alginate, or starch), or a combination thereof.

The nanoparticle may be further modified (e.g., by adding a coating to the exterior surface of the nanoparticle) to improve the efficacy of biological delivery of the nanoparticle. The coating may be selected such that the coating has properties better aligned with biological delivery than the biodegradable matrix. For example, the nanoparticle may include a hydrophilic coating to improve the suspension of the nanoparticle in aqueous media. Alternatively, the nanoparticle may include a coating to reduce electrostatic repulsion between charged nanoparticles. The coating can be made from a biodegradable material. The coating may be, for example, polyglucose sorbitol carboxymethyl ether or polyethylene glycol.

The nanoparticle may include a sub-nanoparticle. A sub-nanoparticle is a defined nanoparticulate structure and may be encapsulated within the biodegradable matrix. A sub-nanoparticle may allow for the incorporation of any materials known in the art (e.g., any contrast agents known in the art) into a nanoparticulate structure without chemical modification to the material. A sub-nanoparticle, therefore, allows for the administration of materials without changing chemical properties. Further, a sub-nanoparticle may reduce or prevent the leakage of a contrast agent from the nanoparticle. The sub-nanoparticle may be substantially spherical, elliptical, rod-shaped, cylindrical, or prismatic or the sub-nanoparticle may be irregularly shaped.

The diameter of the sub-nanoparticle may be from about 1 nm to about 30 nm (e.g., from about 2 nm to about 28 nm, from about 3 nm to about 26 nm, from about 4 nm to about 24 nm, from about 5 nm to about 22 nm, from about 6 nm to about 20 nm, from about 7 nm to about 18 nm, from about 8 nm to about 16 nm, or from about 9 nm to about 14 nm). The diameter of the sub-nanoparticle may be less than about 30 nm (e.g., less than about 28 nm, less than about 26 nm, less than about 24 nm, less than about 22 nm, less than about 20 nm, less than about 18 nm, less than about 16 nm, less than about 14 nm, less than about 12 nm, less than about 10 nm, less than about 9 nm, less than about 8 nm, less than about 7 nm, less than about 6 nm, less than about 5 nm, less than about 4 nm, less than about 3 nm, or less than about 2 nm).

The sub-nanoparticle of the present disclosure may be constructed with or include a matrix material. The matrix material may be a physiologically or pharmaceutically acceptable material and/or a biodegradable material. The material may be, e.g., non-toxic, biocompatible, and/or hydrophilic. Examples of biodegradable matrix materials include: polyglycolide (PGA), polylactide (PLA), poly(lactide-co-glycolide) (PLGA), polycaprolactone (PCL), poly (alkenedicarboxylate) s (e.g., poly(butylene succinate) (PBS), poly(ethylene succinate) (PES), poly(butylene succinate-co-adipate) (PBSA), or poly(p-dioxanone) (PPDO)), polycarbonates (e.g., poly(trimethylene carbonate) (PTMC), poly(propylene carbonate), or poly[oligo(tetramethylene succinate)-co(tetramethylene carbonate)]), aromatic copolyesters (e.g., poly(butylene adipate-co-terephtalate) (PBAT), poly(ethylene terephtalate), Biomax®, Ecoflex®, Origo-Bi®, poly(β-hydroxyalcanoate), xanthan, curdlan, pullulan, poly(hydroxybutyrate) (PHB), or poly(hydroxybutyrate-co-hydroxyvalerate) (PHBV)), polyamides and polypeptides (e.g., aliphatic poly(ester-amide) s, copolymers of 1,2-ethanediol, adipic acid and amino acids (including glycine and phenylalanine), CAMEO®, or BAK 1095®), polyanhydrides (e.g., poly(sebacic anhydride)), polysaccharides e.g., (chitin, chitosan, starch, poly-α-1,4-D-glucopyranoside (amylose), poly-α-1,4-Dglucopyranoside-α-1,6-D-glucopyranoside (amylopectine), cellulose, cellulose esters, cellulose acetate, microcrystalline cellulose, carboxymethylcellulose, lignocellulose, alginic acid, sodium alginate, calcium alginate, hyaluronic acid, or chondroitin sulphate), proteins (e.g., gelatin, gelatine grafts, soy protein, wheat gluten, collagen, elastin, albumine, or fibrin), oils, fatty acids, methyl methacrylate poly(ethyl acrylate), polymer blends (e.g., starch blends (e.g., starch-poly(ethylene-co-vinyl alcohol) (EVOH), starch-polyvinyl alcohol, starch-PLA, starch-PCL, starch-PBS, or starch-PHB), blends of PHBV and PPC, blends of poly(aspartic acid-co-lactide) (PAL) and PLLA, blends of PAL and PBS, or blends of PAL and PCL), poly(propylene fumarate) (PPF), poly(E-caprolactone-fumarate), or any copolymer, block-copolymer, dendrimer, or mixture thereof. Additional biodegradable matrices are known in the art (see, e.g., U.S. Pat. No. 10,058,633; the matrices of which are incorporated herein by reference).

The matrix of the sub-nanoparticle may contain, or include, hyaluronic acid (HA), polyethylene glycol diacrylate (PEGDA), polyglycolic acid (PGA), polylactic acid (PLA), poly(lactic-co-glycolic acid) (PLGA), Collagen, Gelatin, carboxymethyl chitosan (CCN), carboxymethyl cellulose (CMC), a phospholipids, a polysaccharide, or a combination thereof.

The matrices of the nanoparticle and sub-nanoparticle may be the same or different. For example, the biodegradable matrix and sub-nanoparticle matrix may include at least one common component.

A schematic depicting an exemplary nanoparticle of the present disclosure is shown in FIG. 2. FIG. 2A shows a nanoparticle including a plurality of an embedded contrast agent (e.g., iohexol; represented by a star). The iohexol may be localized within a sub-nanoparticle within the nanoparticle. FIG. 2B shows the nanoparticle of FIG. 2A, having been modified to include a coating material (e.g., polyethylene glycol (PEG); represented by a spiral).

The imaging media containing the nanoparticle may be provided in a lyophilized form prior to administration.

Pharmaceutical Compositions

Imaging media of the present disclosure may be prepared, stored and/or administered as a pharmaceutical composition. The pharmaceutical composition includes the imaging media suspended, dispersed, or dissolved in a pharmaceutically acceptable carrier, e.g., water, an alcohol (e.g., ethanol) a polyol (e.g., sorbitol, xylitol, mannitol, erythritol, maltitol, lactitol, isomalt, or glycerol), a polyether (e.g., polyacetal, polyethylene glycol (PEG), polypropylene glycol (PPG), polytetramethylene glycol (PTMG), or poly (epicholorhydrin)), salcaprozate sodium, sodium caprate, or a combination thereof. The excipient may be a buffered carrier (e.g., buffered glycerol, buffered water, buffered saline, or buffered ethanol). Further examples of pharmaceutically acceptable excipients include pharmaceutically acceptable salt solutions (e.g., phosphate solutions), and solutions of organic acids including salt solutions thereof. Examples of these and other pharmaceutically acceptable carriers are described in Remington's Pharmaceutical Sciences (1991, Mack Publication Co., New Jersey), the entirety of which is incorporated herein by reference. The pharmaceutical compositions may be prepared, packaged, or sold in the form of a sterile injectable aqueous or oily suspension or solution. A pharmaceutically acceptable excipient may further include, e.g., dispersing agents, wetting agents, or suspending agents. An imaging media nanoparticle may be lyophilized prior to hydration or solvation with an excipient.

The localization of the contrast agent within the nanoparticle, and the buildup of the imaging media in the liver, allows the imaging media of the present disclosure to be administered at much lower concentrations than what is typically observed in the art. The contrast agent (e.g., iodine) may be present in the pharmaceutical composition at a concentration of from about 5 mg/mL to about 350 mg/ml (e.g., from about 5 mg/mL to about 325 mg/mL, from about 5 mg/mL to about 300 mg/mL, from about 5 mg/ml to about 275 mg/mL, from about 5 mg/mL to about 250 mg/mL, from about 5 mg/mL to about 225 mg/mL, from about 5 mg/mL to about 200 mg/mL, from about 5 mg/ml to about 175 mg/mL, from about 5 mg/ml to about 150 mg/mL, from about 5 mg/mL to about 125 mg/mL, or from about 5 mg/mL to about 100 mg/mL). When the contrast agent (e.g., iodine) is administered for the visualization of the vasculature, the contrast agent may be present in the pharmaceutical composition at a concentration of less than 100 mg/ml (e.g., less than 90 mg/mL, less than 80 mg/mL, less than 70 mg/mL, less than 60 mg/mL, less than 50 mg/mL, less than 40 mg/mL, less than 30 mg/mL, less than 25 mg/mL, less than 20 mg/mL, less than 15 mg/mL, less than 10 mg/mL, or less than 5 mg/mL). When the contrast agent (e.g., iodine) is administered for visualization of the liver, the contrast agent may be present at a concentration of less than 50 mg/ml (e.g., less than 45 mg/mL, less than 40 mg/mL, less than 35 mg/mL, less than 30 mg/mL, less than 25 mg/mL, less than 20 mg/mL, less than 15 mg/mL, less than 10 mg/mL, or less than 5 mg/mL).

Kits

The disclosure also features kits including an imaging media and/or pharmaceutical composition described herein and one or more additional components, e.g., a prepared volume of the pharmaceutically acceptable excipient, a syringe, a puncture set, a package insert, or a mixer. The kit may include the imaging media and/or pharmaceutical composition in bulk, as a single unit dose, or as a plurality of single unit doses. The imaging media may be lyophilized prior to packaging. The kit may include a mixer (e.g., a portable mixer) which stirs a dispersion of the imaging media in the excipient to ensure dissolution. The package insert may instruct the user to mix the imaging media and the excipient using the mixer for an appropriate duration. The kit may also provide components and/or equipment for administering the imaging media and/or pharmaceutical composition described herein. An example may be components or equipment that providing vascular access (e.g., a syringe or a vascular access micro puncture set and access sheath; see, e.g., U.S. Pat. No. 11,027,104, the entirety of which is incorporated by reference). The kit may also include instructions for administering the imaging media and/or a pharmaceutical composition thereof, e.g., in connection with an imaging or an image-guided procedure.

Methods of Use

An imaging media of the present disclosure may be administered to a subject while performing an imaging an image-guided procedure on the subject. A subject may be selected for an imaging procedure as a diagnostic procedure, to aid in a therapeutic procedure, or both.

The imaging media may be administered as a pharmaceutical composition wherein the imaging media has been dispersed in a pharmaceutically acceptable excipient. The imaging media or the pharmaceutical composition may be administered intravenously. The imaging media may be administered intravenously, intraarterially, intrathecally, subcutaneously, or directly to the parenchyma of the site to be imaged. The imaging media may be administered as a single dose or in multiple doses. Each dose may contain the contrast agent (e.g., iodine) at a concentration of from about 5 mg/mL to about 350 mg/ml (e.g., from about 5 mg/mL to about 325 mg/mL, from about 5 mg/mL to about 300 mg/mL, from about 5 mg/mL to about 275 mg/mL, from about 5 mg/mL to about 250 mg/mL, from about 5 mg/mL to about 225 mg/mL, from about 5 mg/mL to about 200 mg/mL, from about 5 mg/ml to about 175 mg/mL, from about 5 mg/mL to about 150 mg/mL, from about 5 mg/mL to about 125 mg/mL, or from about 5 mg/mL to about 100 mg/mL). The imaging media may have a circulation half-life of, e.g., at least 2 hours (e.g., at least 3 hours, at least 4 hours, at least 5 hours, at least 6 hours, or from about 4 hours to about 6 hours) and a liver-residence time of at least 15 minutes (e.g., at least 20 minutes, at least 25 minutes, at least 30 minutes, at least 35 minutes, at least 40 minutes, at least 45 minutes, at least 50 minutes, at least 55 minutes, at least 1 hr, etc.).

After administration, the target site is then imaged by an imaging modality described herein. An image may then be generated of the tissue, wherein the image is colored depending on the value of the measured property (e.g., X-ray attenuation) at different locations in the image. The image is colored depending on the Hounsfield Unit value at different locations in the image.

Methods of Making

An imaging media of the present disclosure may be synthesized using any means known in the art which can synthesize a nanoparticle and then either during synthesis or post synthetically incorporate an additional material, thereby dispersing or embedding the additional material in the biodegradable matrix (e.g., into the nanoparticle core). Exemplary methods include those disclosed in, e.g., International Patent Publication No.: WO 2010/015824; WO 2010/052455; WO 2005/044224; and WO 2009/073193; U.S. Pat. No. 8,207,290; and Plucinski et al., *Polysaccharide Nanoparticles: From Fabrication to Applications, J. Mater. Chem. B,* 2021, 9, 7030; the methods of synthesis of which are incorporated herein by reference. The imaging media may be formed via a microfluidic method (e.g., by contacting a liquid phase including the biodegradable polymer with an antiphase including the contrast agent at a prescribed rate to form a nanoparticle of desired size). The method may allow for nanoparticles of a suitable size (e.g., a diameter of at least 5 nm, at least 10 nm, at least 15 nm, at least 20 nm, at least 25 nm, at least 30 nm, at least 35 nm, at least 40 nm, at least 50 nm, at least 75 nm, at least 100 nm, at least 125 nm, at least 150 nm, at least 175 nm, at least 200 nm, at least 250 nm, at least 300 nm, at least 350 nm, at least 400 nm, at least 450 nm, at least 500 nm, at least 550 nm, at least 600 nm, at least 650 nm, at least 700 nm, at least 800 nm, or at least 900 nm) to be formed. The method may allow for an encapsulation efficiency (e.g., the amount of contrast agent in a reaction mixture incorporated into the nanoparticle) of as high as 99%, with resulting particle polydispersity of less than 1% and a uniform morphology.

A nanoparticle encapsulating a sub-nanoparticle(s) may be formed by first producing a sub-nanoparticle, e.g., using a method described above for producing a nanoparticle, with a diameter of less than 30 nm (e.g., less than about 28 nm, less than about 26 nm, less than about 24 nm, less than about 22 nm, less than about 20 nm, less than about 18 nm, less than about 16 nm, less than about 14 nm, less than about 12 nm, less than about 10 nm, less than about 9 nm, less than about 8 nm, less than about 7 nm, less than about 6 nm, less than about 5 nm, less than about 4 nm, less than about 3 nm, or less than about 2 nm). A method of making a nanoparticle may be modified (e.g., the flow rate of a phase or antiphase in a microfluidic method may be changed) relative to a method described above to create the smaller sub-nanoparticles. As with the nanoparticle described above, a contrast agent may be encapsulated in the sub-nanoparticle with an encapsulation efficiency of as high as 99%. After the sub-nanoparticle has been formed, the sub-nanoparticle may be resuspended in a solvent (e.g., in the aqueous phase of the microfluidic method) described above. By performing the microfluidic method again, now using the sub-nanoparticles as a starting material, the larger nanoparticle may form around the sub-nanoparticle. By including a contrast agent only in the sub-nanoparticle synthesis step, the contrast agent may be localized entirely to the interior of the nanoparticle (i.e., entirely encapsulated by the sub-nanoparticle, with no contrast agent on the exterior or surface of the nanoparticle or in the interior of the nanoparticle other than in the interior of the sub-nanoparticle), which slows, reduces, or inhibits leakage of the contrast agent from the imaging media after the administration to a subject.

EXAMPLES

The following examples are put forth so as to provide those of ordinary skill in the art with a description of how the compositions and methods described herein may be used, made, and evaluated, and are intended to be purely exemplary of the invention and are not intended to limit the scope of the invention.

Example 1

Use of an Imaging Media

A subject with a primary or metastatic liver tumor can be evaluated and determined to be a candidate for image-guided ablation. A dose of an imaging media of the present disclosure can be injected through an IV access site. The imaging media includes a contrast agent (e.g., an iodine containing contrast agent, e.g., iodixanol, iohexol, iohexol related compound B or a derivative thereof, diatrizoic acid or a derivative thereof, or a combination thereof) enclosed within a biodegradable nanoparticle (e.g., a nanoparticle with a matrix of or including hyaluronic acid (HA), polyethylene glycol diacrylate (PEGDA), polyglycolic acid (PGA), polylactic acid (PLA), poly(lactic-co-glycolic acid) (PLGA), Collagen, Gelatin, carboxymethyl chitosan (CCN), carboxymethyl cellulose (CMC), phospholipids, a polysaccharide, or a combination thereof).

Prior to administration, the imaging media may be suspended in a pharmaceutically acceptable excipient such that the concentration of iodine in the pharmaceutical composition is from about 5 mg/ml to about 350 mg/ml (e.g., from about 5 mg/mL to about 100 mg/mL). Following administration, the imaging media would be given time to circulate through a subject and to localize in the liver. At least one CT image of the liver would be obtained. As a result of the imaging media, the contrast of the CT images is enhanced by at least 10 HU and the liver tumor would be visible with clear margins. The resulting CT image is expected to be similar to the image shown in FIG. 1. Because of the long circulation half-life and liver-retention time, a physician could obtain multiple CT images of the tumor if required to further improve the visualization of the tumor.

A physician may then use the previously collected images, or collect new CT images, to aid in treatment. For example, the physician may use the images to guide the placement of one or more ablation probes for use during a tumor ablation procedure. Because of the long liver retention time of the imaging media, the physician would not need to readminister the imaging media during the procedure, reducing the total amount of contrast agent required by the procedure, and reducing the risk of nephrotoxic effects felt by the patient.

Other Embodiments

The foregoing detailed description and examples have been given for clarity of understanding only. No unnecessary limitations are to be understood therefrom. The disclosure is not limited to the exact details shown and described, for variations apparent to one skilled in the art will be included within the disclosure defined by the claims.

Unless otherwise indicated, all numbers expressing quantities of components and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The complete disclosures of all patents, patent applications including provisional patent applications, publications including patent publications and non-patent publications, and electronically available material cited herein are incorporated by reference.

The invention claimed is:

1. An imaging media comprising:
   a) a nanoparticle comprising a diameter of from about 10 nm to about 650 nm and a biodegradable matrix, wherein the biodegradable matrix does not comprise a metal matrix; and
   b) a plurality of sub-nanoparticles encapsulated within an interior of the biodegradable matrix of the nanoparticle, wherein each sub-nanoparticle of the plurality of sub-nanoparticles comprises:
   (i) a biodegradable matrix; and
   (ii) a contrast agent within an interior of the biodegradable matrix of the sub-nanoparticle,
   wherein:
   the contrast agent is a nonionic or ionic contrast agent comprising iodine as the sole contrast agent and the concentration of the contrast agent in the imaging media is from 5 mg of iodine per 1 mL of the imaging media to 200 mg of iodine per 1 mL of the imaging media.

2. The imaging media of claim 1, wherein the biodegradable matrix of the nanoparticle comprises a polymer matrix.

3. The imaging media of claim 2, wherein the polymer matrix is or comprises hyaluronic acid (HA), polyethylene glycol diacrylate (PEGDA), polyglycolic acid (PGA), polylactic acid (PLA), poly(lactic-co-glycolic acid) (PLGA), Collagen, Gelatin, carboxymethyl chitosan (CCN), carboxymethyl cellulose (CMC), phospholipids, a polysaccharide, or a combination thereof.

4. The imaging media of claim 1, wherein the nanoparticle is spherical, elliptical, rod-shaped, cylindrical, prismatic, or irregular.

5. The imaging media of claim 1, wherein the nanoparticle further comprises a coating on the exterior surface of the biodegradable matrix.

6. The imaging media of claim 5, wherein the coating is hydrophilic.

7. The imaging media of claim 5, wherein the coating is a polymer coating.

8. The imaging media of claim 7, wherein the polymer coating is polyglucose sorbitol carboxymethyl ether or polyethylene glycol (PEG).

9. The imaging media of claim 5, wherein the coating is from about 1 nm to about 100 nm thick.

10. The imaging media of claim 1, wherein the biodegradable matrix of the sub-nanoparticle comprises hyaluronic acid (HA), polyethylene glycol diacrylate (PEGDA), polyglycolic acid (PGA), polylactic acid (PLA), poly(lactic-co-glycolic acid) (PLGA), Collagen, Gelatin, carboxymethyl chitosan (CCN), carboxymethyl cellulose (CMC), phospholipids, a polysaccharide, or a combination thereof.

11. The imaging media of claim 1, wherein the sub-nanoparticle and the nanoparticle comprise an identical material.

12. The imaging media of claim 1, wherein the sub-nanoparticle is spherical, elliptical, rod-shaped, cylindrical, prismatic, or irregular.

13. The imaging media of claim 1, wherein the sub-nanoparticle is substantially spherical and the diameter of the sub-nanoparticle is from about 1 nm to about 30 nm.

14. The imaging media of claim 1, wherein the contrast agent is a nonionic contrast agent selected from iodixanol, iohexol, iohexol related compound B, diatrizoic acid, or a combination thereof.

15. The imaging media of claim 1, wherein the contrast agent is an ionic contrast agent selected from the group consisting of a diatrizoate salt or an iothalamate salt.

16. A pharmaceutical composition comprising the imaging media of claim 1 and a pharmaceutically acceptable excipient.

17. The pharmaceutical composition of claim 16, wherein the excipient is a polyol, a polyether, salcaprozate sodium, or sodium caprate, and wherein the polyether is polyethylene glycol.

18. A method of imaging biological tissue in a subject comprising administering to the subject the imaging media of claim 1 or a pharmaceutical composition comprising the imaging media and detecting the imaging media in the biological tissue.

19. The method of claim 18, wherein the biological tissue is an organ, wherein the organ is the liver.

20. The method of claim 18, wherein the imaging media or pharmaceutical composition is administered directly to the biological tissue or administered intravascularly.

21. The method of claim 18, wherein the detecting comprises using X-ray imaging, wherein the X-ray imaging is fluoroscopy or computed tomography (CT) imaging.

22. The method of claim 21, wherein the imaging media provides an image contrast of at least 10 Hounsfield units in the biological tissue relative to imaging performed in the absence of the imaging media.

23. The method of claim 18, further comprising mixing the imaging media and an excipient at the time of administration.

24. The method of claim 18, wherein the nanoparticle is provided as a lyophilized powder, and the method further comprises hydrating, suspending, or solvating the nanoparticle prior to administration.

25. A kit comprising the imaging media of claim 1 or a pharmaceutical composition thereof.

26. The kit of claim 25, wherein the imaging media and the excipient are provided separately and the imaging media is provided as a lyophilized powder.

27. The kit of claim 25, further comprising a mixer and/or a puncture set.

28. The pharmaceutical composition of claim 16, wherein the iodine is present in the pharmaceutical composition at a concentration from about 5 mg/mL to about 100 mg/mL.

* * * * *